United States Patent [19]
Shiber

[11] Patent Number: 6,106,538
[45] Date of Patent: Aug. 22, 2000

[54] METHOD FOR FORMING AN INTERNAL CORONARY BYPASS

[76] Inventor: Samuel Shiber, 365 Kearney Cir., Manchester, N.H. 03104

[21] Appl. No.: 09/286,218

[22] Filed: Apr. 5, 1999

Related U.S. Application Data

[63] Continuation-in-part of application No. 08/904,972, Aug. 1, 1997, abandoned, which is a continuation-in-part of application No. 08/516,772, Aug. 17, 1993, Pat. No. 5,653,696, which is a continuation-in-part of application No. 08/107,453, Aug. 17, 1993, Pat. No. 5,443,443, which is a continuation-in-part of application No. 07/913,231, Jul. 14, 1992, Pat. No. 5,334,211, which is a continuation-in-part of application No. 07/662,558, Feb. 28, 1991, Pat. No. 5,306,244, which is a continuation-in-part of application No. 07/499,726, Mar. 27, 1990, Pat. No. 5,135,531, which is a continuation-in-part of application No. 07/350,020, May 12, 1989, Pat. No. 4,979,939, which is a continuation-in-part of application No. 07/326,967, Mar. 22, 1989, Pat. No. 4,957,482, which is a continuation-in-part of application No. 07/324,616, Mar. 16, 1989, Pat. No. 5,007,896, which is a continuation-in-part of application No. 07/323,328, Mar. 13, 1989, Pat. No. 5,002,553, and a continuation-in-part of application No. 07/332,497, Mar. 13, 1989, Pat. No. 5,024,651, which is a continuation-in-part of application No. 07/286,509, Dec. 19, 1988, Pat. No. 4,894,051, which is a continuation-in-part of application No. 07/243,900, Sep. 13, 1988, Pat. No. 4,886,490, which is a continuation-in-part of application No. 07/225,880, Jul. 29, 1988, Pat. No. 4,842,579, which is a continuation-in-part of application No. 07/205,479, Jun. 13, 1988, Pat. No. 4,883,458, which is a continuation-in-part of application No. 07/078,042, Jul. 27, 1987, Pat. No. 4,819,634, which is a continuation-in-part of application No. 07/018,083, Feb. 24, 1987, Pat. No. 5,041,082, which is a continuation-in-part of application No. 06/874,546, Jun. 16, 1986, Pat. No. 4,732,154, which is a continuation-in-part of application No. 06/609,846, May 14, 1984, abandoned.

[51] Int. Cl.$^7$ ................................................. A61B 17/14
[52] U.S. Cl. ........................... 606/184; 128/898; 600/567
[58] Field of Search .................................... 606/170, 159, 606/184, 180, 151, 129; 600/567; 623/3.1, 11.1; 128/898

[56] References Cited

U.S. PATENT DOCUMENTS

| | | | |
|---|---|---|---|
| 5,018,530 | 5/1991 | Rank et al. | 600/567 |
| 5,488,958 | 2/1996 | Topel et al. | 600/567 |
| 5,762,069 | 6/1998 | Kelleher et al. | 606/129 |

*Primary Examiner*—Michael Buiz
*Assistant Examiner*—Kevin Truong
*Attorney, Agent, or Firm*—Samuel Shiber

[57] ABSTRACT

An internal coronary bypass, for circumventing an obstruction in a coronary artery, having a conduit through the heart's muscle that preferably connects a left-chamber of the heart to the coronary artery, at a point which is downstream of the obstruction, and a one way valve disposed in said conduit allowing blood to flow only in a direction from the left chamber to the artery.

4 Claims, 1 Drawing Sheet

METHOD FOR FORMING AN INTERNAL CORONARY BYPASS

CROSS REFERENCE TO OTHER APPLICATIONS

This application is a continuation in part (CIP) of Appl. 08/904,972 filed Aug. 1, 1997 (now abandoned) which is a CIP of appl. 08/516,772 filed Aug. 17, 1993 (CT17 now U.S. Pat. No. 5,653,696) which is a CIP of appl. 08/107,453 filed Aug. 17, 1993 (CT16 now U.S. Pat. No. 5,443,443) which is a CIP of appl. 07/913,231 filed Jul. 14, 1992 (CT15 now U.S. Pat. No. 5,334,211) which is a CIP of appl. 07/662,558 filed Feb. 28, 1991 (CT14 now U.S. Pat. No. 5,306,244) which is a CIP of appl. 07/499,726 filed Mar. 27, 1990 (CT13 now U.S. Pat. No. 5,135,531) which is a CIP of appl. 07/350,020 filed May 12, 1989 (CT12 now U.S. Pat. No. 4,979,939) which is a CIP of four applications:

Appl. 07/326,967 filed Mar. 22, 1989 (CT11 now U.S. Pat. No. 4,957,482), appl. 07/324,616 filed Mar. 16, 1989 (CT10 now U.S. Pat. No. 5,007,896), appl. 07/323,328 filed Mar. 13, 1989 (CT9 now U.S. Pat. No. 5,002,553) and appl. 07/332,497 filed Mar. 13, 1989 (CT8 now U.S. Pat. No. 5,024,651).

These four applications are CIPs of appl. 07/286,509 filed Dec. 19, 1988 (CT7 now U.S. Pat. No. 4,894,051) which is a CIP of appl. 07/243,900 filed Sep. 13, 1988 (CT6 now U.S. Pat. No. 4,886,490), which is a CIP of three applications:

Appl. 07/225,880 filed Jul. 29, 1988 (CT5 now U.S. Pat. No. 4,842,579) including Reexamination Request 90/003,608 filed Oct. 19, 1994 (now Reexamination Certificate 2711th issued on Oct. 31, 1995), appl. 07/205,479 filed Jun. 13, 1988 (CT4 now U.S. Pat. No. 4,883,458), and appl. 07/078,042 filed Jul. 27, 1987 (CT3 now U.S. Pat. No. 4,819,634).

These three applications are CIPs of appl. 07/018,083 filed Feb. 24, 1987 (CT2 now U.S. Pat. No. 5,041,082) which is a CIP of appl. 06/874,546 filed Jun. 16, 1986 (CT1 now U.S. Pat. No. 4,732,154) which is a CIP of appl. 06/609,846 filed May 14, 1984 (CT0 now abandoned).

All the above applications (and Reexamination materials) are being incorporated herein by reference.

BACKGROUND AND OBJECTIVES OF THE INVENTION

With age, a large percentage of the population develops atherosclerotic arterial obstructions resulting in diminished blood circulation. The disturbance to the blood flow that these obstructions cause may induce blood clots which further block the blood flow. When this process occurs in the coronary arteries, which serve the heart muscle, it is referred to as a "heart attack".

The coronary arteries are generally located on the outer surface of the heart. An established method to overcome the problem is to surgically graft a bypass made of the patient's own vein. The bypass connects the aorta to the artery at a point which is downstream of the obstruction. Such a bypass supplies oxygenated blood to the previously obstructed section of the artery and to the portion of the heart muscle which is served by it.

Grafting a bypass usually entails a major surgery that frail patients often can not endure, additionally, it is an expensive and traumatic procedure.

An objective of the present invention is to provide an internal bypass (i.e., a bypass formed inside the heart rather than outside the heart) through the left-chamber's wall to a point along the obstructed artery which is downstream of the obstruction.

A further objective is to provide an internal bypass which can be placed in the left-chamber's wall through the vascular system without requiring major surgery.

These and other objectives of the invention will become apparent from the following discussion and the accompanying drawings.

DETAILED DESCRIPTION OF THE DRAWINGS

Figure 1:
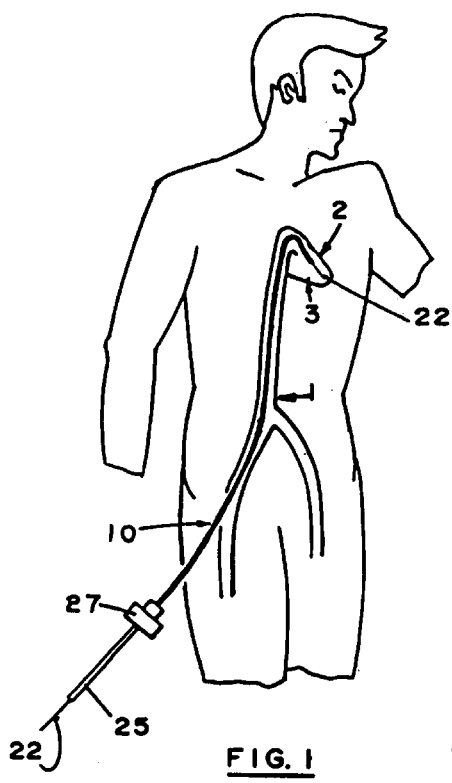
FIG. 1 generally shows a system, inserted at a patient's groin area through the skin, through the patient's arterial system, into a patient's heart for forming an internal bypass according to the present invention.

FIG. 1 generally shows a system 10 inserted at the groin area through the skin, through a patient's arterial system 1, into a left chamber 2 of the patient's heart 3 to form in the heart's muscle a conduit. The conduit originates in the left chamber and feeds the heart's muscle directly or through a coronary artery to which it connects.

Figure 2:
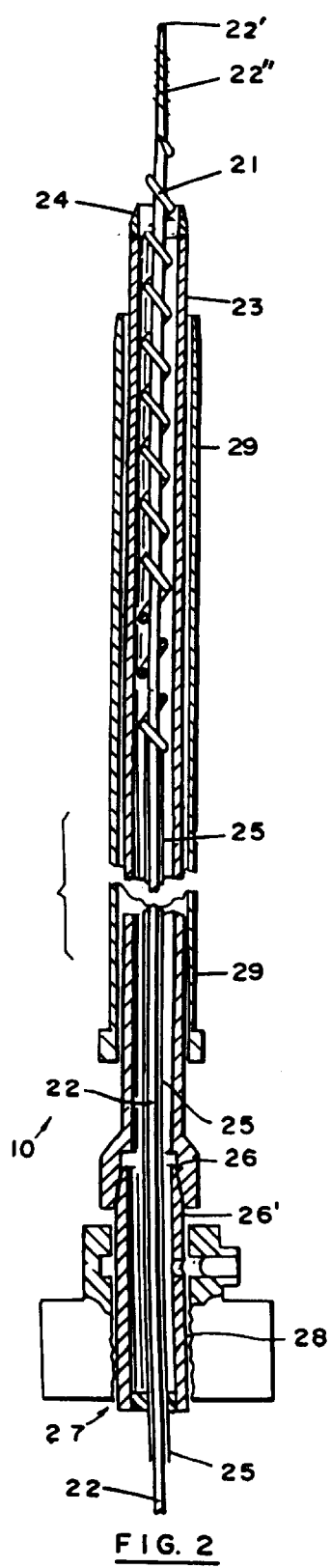
FIG. 2 shows a system (with the middle portion removed due to size limitations on the drawing sheet) for forming the internal bypass.

FIG. 2 shows the system 10 (that utilizes design concepts that have been taught in my above referenced patent applications and patents) for forming a conduit 35 through the heart's muscle by engaging and removing a plug shaped portion of a heart's muscle and optionally placing a one way valve in the conduit.

The main components of the system 10 are: a flexible helical wire 21 slideable over a guidewire 22 (throughout the FIGURES same numerals refer to similar items) and flexible catheter 23 slideable over the helical wire. The system is disposed in a guiding catheter 29. The flexible catheter has a coring means in the form of a tubular blade 24 at its distal end. The helical wire is attached to a thin walled stainless steel extension tube 25 (alternatively the helical wire can be continued, instead of the extension tube or, the extension may be constructed from wound metal ribbons like the catheters shown in my above referenced patent No. 4,819,634). Coupling means in the form of a tapered seat 26 couples the flexible catheter to a drive means in the form of a motor 27 having the hollow shaft 28 with a matching tapered end 26'.

The guidewire 22 can incorporate an ultrasound probe adapted to emit and receive ultrasound waves through its tip 22' and generate on a monitor (not shown) connected to the proximal end of the guidewire, a picture of the tissues surrounding the tip 22'. The proximally adjacent section of the guidewire 22" is shaped like a screw for inserting it and screwing it into the heart muscle.

Figure 3:
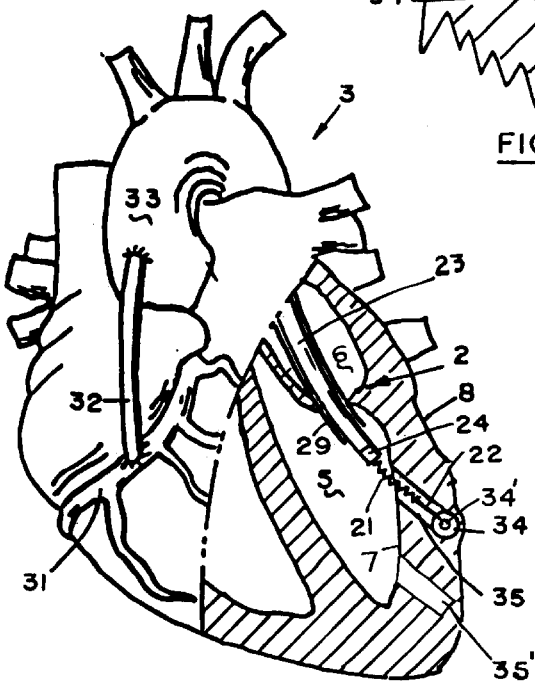
FIG. 3 generally shows a heart with An external bypass vein graft, shown for reference, which circumvents an obstruction (not shown) in a first coronary artery by connecting a point along the artery which is downstream of the obstruction to the aorta, and, an internal coronary bypass according to the present that is formed through the heart's muscle and contains a one way valve.

FIG. 3 generally shows a heart 3 with a first coronary artery 31 which is obstructed by atherosclerotic plaque (plaque not shown) and a conventional external bypass graft 32 which connects the aorta 33 to the first coronary artery at a point which is downstream of the obstruction. A second coronary artery 34, (shown cross-sectioned) is also obstructed by atherosclerotic plaque (plaque not shown) and the obstruction is circumvented by an internal bypass in the form of a conduit 35 which connects a left-chamber 2 of the heart to the second artery at a point which is downstream of the obstruction.

An ultrasound emitting guidewire 34' (shown cross-sectioned) can optionally be inserted into the artery 34 to assist the physician in directing the guidewire 22 towards the artery 34.

An alternative internal bypass in the form of a conduit 35' also originates at the left-chamber 2 and feeds the heart muscle directly.

Throughout this application the term "left-chamber" denotes the left ventricle 5 or the left atrium 6, either of which contain oxygenated blood. The inner surface of the left chamber is marked with numeral 7 and the outer surface 8.

Figure 4:
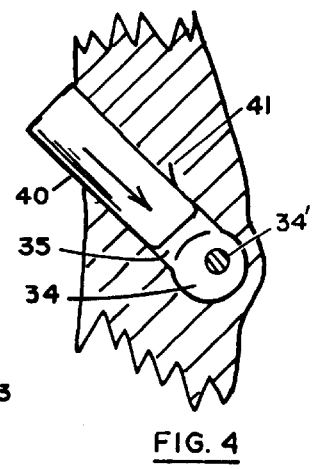
FIG. 4 shows the placement of a one way valve in the internal coronary bypass for allowing flow only in one direction, i.e., from the left chamber to the artery.

FIG. 4 shows a one way valve 40 disposed in the conduit 35. The valve 40 allows blood to flow from the left chamber to the artery 34 but blocks flow in the opposite direction. Anchors 41 (one shown) engage with the surrounding conduit wall, i.e., the surrounding heart muscle to affix the valve in the conduit.

After the components of the system 10 are inserted into the heart through the vascular system, using conventional techniques, the guidewire 22, that preferably incorporates an ultrasound probe, emits and receives ultrasound waves through its tip 22' and enables the physician to locate, from inside the heart's left chamber, the artery 34 at which point the physician rotates, and thereby inserts and screws the distal section 22" into the heart muscle. The flexible helical wire 21 is then rotated and slid over the guidewire to screw into the heart muscle and then the flexible catheter 23 and the tubular blade 24 are rotated and slid over the flexible helical wire to core and envelope a plug shaped portion of the heart muscle. The flexible helical wire 21 is then pulled back with the plug leaving a conduit 35 which connects the left chamber and artery 34. The guiding catheter 29 and/or the guidewire 22 can be left in place to facilitate the subsequent insertion of the one way valve 40 which can be delivered through the guiding catheter 29 into the conduit 35 where the anchors 41 engage with the surrounding heart muscle to affix the valve in the conduit 35.

A conduit 35' can be similarly formed to feed directly small vessels and tissue that are opened and exposed while the conduit is formed. The conduit 35' does not intersect with a specific coronary artery and is therefor easier to place.

The conduit 35' can be formed as follows:

Inserting, over the guidewire 22, a flexible helical wire 21 into the heart's left chamber and screwing it into the heart's muscle from inside the heart through the inner surface of the left chamber as marked with numeral 7 and stopping short of the outer surface marked 8, rotating and advancing a flexible catheter 23, having a tubular blade 24 at its distal tip, over the flexible helical wire 21, to core from inside the heart a plug shaped portion of the heart muscle into which the helical wire has been screwed and envelop the plug shaped portion, and, pulling back the flexible helical wire with the plug leaving a conduit 35' that originates in the left chamber and brings oxygenated blood small blood vessels and muscle tissue that have been opened and exposed in the process of forming the conduit.

Optionally the guidewire 22 and can be inserted and screwed into the heart's muscle, from inside the heart, along a trajectory that intersects with a coronary artery 34 on the heart's outer surface at a point along the coronary artery which is downstream of the obstruction and then rotating, and, advancing a flexible catheter until its tubular blade cuts into the coronary artery to form a conduit 35 that connects the heart's left chamber to the coronary artery 34. A one way valve can be disposed in the conduit to allow blood to flow from the left chamber to the coronary artery but not in the opposite direction to.

Modifications and substitutions can be made without departing from the spirit of the invention or the scope of the claims:

1. A method for forming an internal coronary bypass in the heart's muscle comprising the following steps:

Inserting, over a guidewire, a flexible helical wire into the heart's left chamber and screwing it into the heart's muscle from inside the heart, rotating and advancing a flexible catheter, having a tubular blade at its distal tip, over the flexible helical wire, to core from inside the heart a plug shaped portion of the heart muscle into which the helical wire has been screwed and envelop the plug shaped portion, pulling back the flexible helical wire with the plug.

2. A method for forming an internal coronary bypass in the heart's muscle comprising the following steps:

Inserting a wire into the heart's muscle, from inside the heart, along a trajectory that intersects with a coronary artery at a point along the coronary artery which is downstream of the obstruction, rotating and advancing a flexible catheter, having a blade at its distal tip, over the wire into the heart muscle and into the coronary artery thereby cutting a plug shaped portion of the heart muscle and the wall of the coronary artery to establish an internal coronary bypass between the left chamber and the coronary artery.

3. As in claim 2, further comprising the step of placing a one way valve in said conduit to allow blood to flow from the left chamber to the coronary artery but not allow flow in the opposite direction.

4. A method for forming an internal coronary bypass in the heart's muscle comprising the following steps:

Inserting, over a guidewire, a flexible helical wire into the heart's left chamber, screwing the flexible helical wire into the heart's muscle from inside the heart along a trajectory that intersects with a coronary at a point along the coronary artery which is downstream of the obstruction, rotating and advancing a flexible catheter, having a tubular blade at its distal tip, over the flexible helical wire, to core from inside the heart a plug shaped portion of the heart muscle with which the helical wire is engaged until the tubular blade cuts into the coronary artery, and envelop the plug pulling back the flexible helical wire with the plug.

* * * * *